United States Patent [19]

Callingham et al.

[11] 4,264,586

[45] Apr. 28, 1981

[54] ANTIPERSPIRANT EMULSION

[75] Inventors: Martin Callingham, London; Philomena Finnerty, Brentford, both of England

[73] Assignee: Lever Brothers Company, New York, N.Y.

[21] Appl. No.: 910,556

[22] Filed: May 30, 1978

Related U.S. Application Data

[63] Continuation of Ser. No. 762,615, Jan. 26, 1977, abandoned.

[30] Foreign Application Priority Data

Jan. 28, 1976 [GB] United Kingdom ............... 3295/76

[51] Int. Cl.$^3$ .......................... A61K 7/32; A61K 7/38
[52] U.S. Cl. ....................... 424/68; 424/47; 424/65; 424/66; 424/67; 424/168; 424/184
[58] Field of Search ................. 424/65, 68, 184, 168

[56] References Cited

U.S. PATENT DOCUMENTS

| | | | |
|---|---|---|---|
| 2,145,583 | 1/1939 | Carlson | 424/65 X |
| 3,485,915 | 12/1969 | Gerstein et al. | 424/65 X |
| 3,708,435 | 1/1973 | Starkman | 424/67 X |
| 3,836,647 | 9/1974 | Lange | 424/184 |
| 3,956,352 | 5/1976 | Bouillon et al. | 424/47 X |
| 4,073,880 | 2/1978 | Pader et al. | 424/66 |
| 4,113,852 | 9/1978 | Kenkare et al. | 424/68 |

FOREIGN PATENT DOCUMENTS

| | | | |
|---|---|---|---|
| 829873 | 12/1969 | Canada | 424/184 |
| 885716 | 6/1943 | France | 424/184 |
| 48-19941 | 6/1973 | Japan | 424/184 |

OTHER PUBLICATIONS

Tajkowski et al. Proceedings of Scientific Section, Toilet Goods Assn, No. 20, 12/1953, pp. 1 to 7.
Plein et al. Journ. of the Amer Pharm Assoc., 1953, vol. 42, No. 2, pp. 79 to 85.
Freeman Silicones An Introduction to their Chemistry & Applications, pp. 20 to 23.

Primary Examiner—Dale R. Ore
Attorney, Agent, or Firm—Michael J. Kelly; James J. Farrell; Melvin H. Kurtz

[57] ABSTRACT

An antiperspirant liquid composition in the form of an emulsion comprises a volatile polydimethylsiloxane, a wax, an antiperspirant agent, an emulsifier and water. The wax is first dissolved in the polydimethylsiloxane and then emulsified with the remaining ingredients. The composition can be sprayed on the skin yet is thick enough not to form runs or dribbles on the skin under the influence of gravity.

14 Claims, No Drawings

ANTIPERSPIRANT EMULSION

This is a continuation of application Ser. No. 762,615, filed Jan. 26, 1977, now abandoned.

The invention relates to antiperspirant liquid compositions which are particularly suitable for application to the skin in the form of a spray.

Antiperspirant compositions, which are intended to be dispensed in spray form from, for example a pressurised pack device such as an aerosol can, or a container fitted with a finger-operated pump, or a plastic squeeze bottle fitted with a spray nozzle, can suffer from the disadvantage that in use the antiperspirant composition when sprayed onto the skin forms runs on the skin away from the area of application. This problem is particularly noticeable with antiperspirant compositions containing a proportion of water. Attempts have been made to overcome this problem by the incorporation into such composition of thickeners in an amount sufficient to prevent running, but no really satisfactory solution has been found. For example, use of a polymeric thickener, such as hydroxyethyl cellulose, tends to interfere with atomisation so that a finely-divided spray is not obtained; a clay, such as montmorillonite clay, if used for this purpose tends to flocculate in the presence of a high concentration of electrolyte such as that derived from an antiperspirant agent for example aluminium chlorhydrate and again, a finely divided spray is difficult to obtain.

It has now been discovered that aqueous antiperspirant compositions for dispensing in spray form can be satisfactorily thickened by the incorporation of a volatile polydimethylsiloxane containing dissolved wax. Thickening is achieved by emulsifying the mixed ingredients in the presence of an emulsifying agent.

It has furthermore been demonstrated that these polydimethylsiloxanes, which also have emollient properties, volatilise rapidly from the skin after application of the antiperspirant composition, and for this reason are not retained by the skin as are other oily emollients such as isopropyl myristate commonly found in antiperspirant products. Accordingly, the volatile polydimethylsiloxanes are generally not implicated in the staining of clothing adjacent the treated area as are non-volatile oily emollients.

According to the invention, there is provided an antiperspirant liquid composition, comprising by weight of the composition from 2% to about 60% of a volatile polydimethylsiloxane, from 0.1% to about 30% wax dissolved in the polydimethylsiloxane, from 0.2% to about 40% of an antiperspirant agent, from 0.5% to about 10% of emulsifier and water.

By "thickened" we mean that the composition has a viscosity or a yield point which is sufficiently high to enable the liquid composition to be applied to the skin to be treated, for example the axilla, without the formation of runs or dribbles, under the influence of gravity, away from the point of application. The viscosity or yield point should, however, not be so high that application in the form of a spray is impossible.

The polydimethylsiloxanes that are particularly suitable for the invention are those which are volatile in that they will evaporate rapidly from a thin film of the material at body temperature. The polydimethylsiloxanes that meet these requirements are those that have a viscosity of from 0.5 to 6 centistokes. These may be used individually or in combination with other silicone fluids that have a viscosity in this range. If desired, in addition to the silicone fluids having a viscosity within this range, there may also be incorporated other silicone fluids that have a viscosity higher than 6 centistokes. Care must be taken in this case that not too much of the other silicone fluids are present so as to deleteriously effect the composition.

The polydimethylsiloxanes that are used in the present invention may be either linear polymers or cyclic polymers. When a mixture of polydimethylsiloxanes is employed, some of the polymers may be linear and others may be cyclic.

The linear polydimethylsiloxanes have the following structural formula:

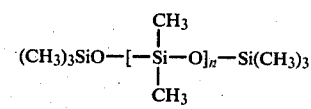

where n is an integer, preferably of from 1 to 5.

Preferred linear polydimethylsiloxanes according to the invention are those having the above formula wherein the integer is 2, 3 or 4.

Examples of suitable linear polydimethylsiloxanes are the three DOW CORNING products known as DC 200 fluids, having viscosities of 0.65, 1.0 and 5.0 centistokes.

The cyclic polydimethylsiloxanes having the following structural formula:

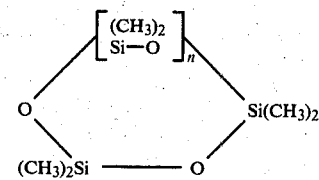

where n is an integer, preferably of from 1 to 4.

The cyclic polydimethylsiloxanes are exemplified by the tetramer which has the following formula:

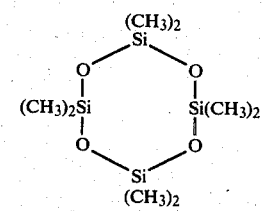

The viscosity of the tetramer is 2.5 centistokes.

Further suitable examples of the cyclic polydimethylsiloxanes are the corresponding trimer, pentamer and hexamer or mixtures of these polymers which have viscosities within the range of from 0.5 to 6 centistokes.

Preferred cyclic polydimethylsiloxanes according to the invention contain a major proportion of the tetramer. Examples of commercially available cyclic polydimethylsiloxanes which generally consist of a mixture of these polymers, with the tetramer predominating are DOW CORNING F 218 FLUID (DOW CORNING is a trade mark) supplied by Dow Corning Corporation, and VOLATILE SILICONE 7207 supplied by Union Carbide Corporation. VOLATILE SILICONE 7158, believed to comprise mainly the pentamer, can also be used.

It is to be understood that the invention is not restricted solely to these examples of commercially available polydimethylsiloxane.

The proportion of polydimethylsiloxane to be incorporated in the antiperspirant composition will normally be from 2% to about 60% by weight of the composition.

The preferred proportion of polydimethylsiloxane is from 5% to 40% by weight of the composition.

Use of less than 2% by weight of the polydimethylsiloxane will result in an antiperspirant composition that is unsufficiently thickened when emulsified so that when sprayed onto the skin, the composition will be sufficiently mobile to form runs. For this reason, antiperspirant compositions containing less than 2% by weight of the polydimethylsiloxane are hereby disclaimed.

Use of more than about 60% by weight of the polydimethylsiloxane is unlikely to contribute further to the thickening or to any other advantageous attribute of the composition.

The waxes that are particularly suitable for the invention are nonionic in character and comprise either (i) a $C_{10}$–$C_{22}$ alkyl fatty alcohol having an average of from 0 to 50 ethylene oxide residues in the molecule, or (ii) a $C_{10}$–$C_{22}$ alkyl ethoxylated fatty acid containing an average of from 1 to 50 ethylene oxide residues in the molecule, or (iii) a triglyceride in which the esterifying acid is a $C_{10}$–$C_{22}$ alkyl fatty acid. Preferred waxes are fatty alcohols and ethoxylated fatty acids.

Examples of waxes are lauryl alcohol, myristyl alcohol, stearyl alcohol, palmityl alcohol, cetyl alcohol, linoleyl alcohol, linolenyl alcohol, ricinoleyl alcohol, arachadecyl alcohol, COSMOWAX (a mixture of fatty alcohols and ethoxylated fatty alcohols manufactured by Croda Chemicals Ltd), POLAWAX (an ethoxylated stearyl alcohol), ethoxylated fatty acids such as polyethylene glycol monostearate and JAPAN WAX (mainly tripalmitin plus 5% glycerol ester dibasic acid manufactured by A F Suter & Co Ltd.). It is to be understood, however, that the invention is not restricted solely to these examples of waxes.

The proportion of the wax to be incorporated in the antiperspirant composition will normally be from 0.1 to about 30% by weight of the composition.

Use of less than 0.1% by weight of the wax will result in an antiperspirant composition that is insufficiently thickened when emulsified, so that when sprayed onto the skin, the composition will be sufficiently mobile to form runs. Use of more than about 30% by weight of the wax is unlikely to contribute further to the thickening or to any other advantageous attribute of the composition.

Whereas the amounts of polydimethylsiloxane and wax in the antiperspirant composition can vary over a wide range as defined, the weight ratio of the siloxane to the wax employed is preferably from 1:1 to 60:1, depending upon the form of the end product. Use of proportions of the siloxane to the wax which are greater than 60:1 can lead to the production of liquid antiperspirant compositions which are insufficiently thickened to be retained on the skin at the point of application and may accordingly form runs or dribbles.

The antiperspirant agents that are particularly suitable for the invention are astringent metal salts, especially aluminium salts. The preferred aluminium salt is aluminium chlorhydrate. Grades of aluminium chlorhydrate which are particularly suitable are those sold under the trade name "CHLORHYDROL" by the Reheis Chemical Company. Other suitable astringent metal salts include those of zirconium and zinc. Further examples are aluminium chloride, aluminium sulphate, aluminium oxychloride, aluminium oxysulphate, zirconium hydroxy chloride, zirconium oxychloride, zinc sulphate and zinc sulphocarbonate. Yet further examples are the polymeric zirconium compounds and complexes described in Netherlands Patent Application 7 501 279 and the polymeric aluminium compounds described in British Patent Application No. 1401/76.

It is also possible to employ as antiperspirant agents moisture absorbent non-astringent polymeric materials, such as those which are the subject of Netherlands Patent Applications Nos 7 414 561 and 7 502 843. These include certain polysaccharides, polypeptides vinyl carboxy polymers and copolymers. Examples of preferred polymers can conveniently be classified as follows:

(a) Water soluble polymers (i) of natural origin: carragheenates, starches guar gum, locust bean gum, low methoxy pectins, agar, furcellaran, xanthan gum, gelatin.

(ii) of synthetic origin: hydroxypropylmethyl cellulose, sodium carboxymethyl cellulose, polyvinylalcohol (such as Elvanol), polyethylene oxides, polyvinylpurrolidone, carboxyvinyl polymers (such as Carbopol), copolymers of methyl vinyl ether and maleic anhydrides, linear ionenes.

(b) Water insoluble polymers (i) of natural origin: mixed salts of calcium and sodium alginate, crosslinked dextrans, chemically modified cellulose, microcrystalline cellulose, calcium alginate, alginic acid, pregelatinized starches, chemically modified starches—especially those identified and prepared by the methods set out in U.S. Pat. No. 3,002,823; and starch copolymers such as hydrolysed (particularly based-hydrolysed starch—polyacrylonitrile graft copolymers identified and prepared by the methods set out in Journal of Applied Polymer Science, Volume 13, pages 2007–2017 (1969), and Volume 15, pages 3015–3024.

(ii) of synthetic origin: crosslinked polyacrylamides, crosslinked polyacrylic acids, crosslinked polyhydroxyethyl methacrylate, crosslinked polyvinyl alcohol, crosslinked polyvinylpurrolidone, sulphonated polystyrene crosslinked with divinylbenzene, quaternized polyvinyl puridine crosslinked with divinyl benzene, crosslinked or branched ionenes. These moisture absorbent materials when deposited on the skin, function to absorb moisture such as perspiration as it exudes onto the skin surface. It is furthermore possible to employ mixtures of astringent and non-astringent antiperspirant agents.

Although any antiperspirant agent can be employed in particulate form in the composition, the benefits of the invention can best be appreciated where the antiperspirant agent is in a dissolved state in the composition and is intended for spraying as a solution onto the skin.

The proportion of the antiperspirant agent to be incorporated in the antiperspirant composition is very much a matter of choice, dependant on the effectiveness of a chosen antiperspirant agent, the needs of the consumer and the nature of the device from which it is to be dispensed. In general, however, the antiperspirant agent will normally form from 0.2 to about 40%, preferably from 3 to 25% and most preferably from 5 to 20% by weight of the composition.

The choice of a suitable emulsifier for the invention for emulsifying the polydimethylsiloxane/wax solution with water to form the aqueous antiperspirant composition will depend on the nature of the end product and more specifically on whether the product is to be in the form of an oil-in-water emulsion or a water-in-oil emulsion.

It can be stated generally that the effectiveness of an emulsifier in emulsifying a particular mixture of an oily substance and water will depend on the hydrophylic-lyophylic balance (HLB) value of the emulsifier. For a full discussion on the relevance of the HLB values of emulsifiers see "Emulsions: Theory and Practice" by Paul Becher (1965) at page 231 et seq.

It will be appreciated that emulsifiers of differing HLB values can be mixed to give an emulsifier mixture which has an effective HLB value between the HLB values of its constituent emulsifiers. Accordingly, reference herein to "an emulsifier" includes mixtures of emulsifiers.

Experiments have shown that for emulsifying polydimethylsiloxane and water, an emulsifier having an HLB value of from about 10.5 to about 13.0, preferably about 11.5 is required to form an oil-in-water emulsion. If, however, a water-in-oil emulsion is required, the HLB value of the emulsifier should be from about 6.5 to about 8.6, preferably about 7.5.

Examples of individual emulsifiers with their appropriate HLB values falling within these ranges are given in the following table.

| Emulsifiers for "water-in-oil" emulsions | | |
|---|---|---|
| Name | Chemical Designation | Value |
| Glaurin | Diethylene glycol monolaurate (soap free) | 6.5 |
| Span 40 | Sorbitan monopalmitate | 6.7 |
| Arlacel 40 | Sorbitan monopalmitate | 6.7 |
| Atlas G-2242 | Polyoxyethylene dioleate | 7.5 |
| Atlas G-2147 | Tetraethylene glycol monostearate | 7.7 |
| Atlas G-2140 | Tetraethylene glycol monooleate | 7.7 |
| Atlas G-2800 | Polyoxypropylene mannitol dioleate | 8 |
| Atlas G-1493 | Polyoxyethylene sorbitol lanolin oleate derivative | 8 |
| Atlas G-1425 | Polyoxyethylene sorbitol lanolin derivative | 8 |
| Atlas G-3608 | Polyoxypropylene stearate | 8 |
| Span 20 | Sorbitan monolaurate | 8.6 |
| Arlacel 20 | Sorbitan monolaurate | 8.6 |

| Emulsifiers for "oil-in-water" emulsions | | |
|---|---|---|
| Name | Chemical Designation | Value |
| Tween 65 | Polyoxyethylene sorbitan tri-stearate | 10.5 |
| Atlas G-3705 | Polyoxyethylene lauryl ether | 10.8 |
| Tween 85 | Polyoxyethylene sorbitan tri-oleate | 11 |
| Atlas G-2116 | Polyoxyethylene oxypropylene oleate | 11 |
| Atlas G-1790 | Polyoxyethylene lanolin derivative | 11 |
| Atlas G-2142 | Polyoxyethylene monooleate | 11.1 |
| Myrj 45 | Polyoxyethylene monostearate | 11.1 |
| Atlas G-2141 | Polyoxyethylene monooleate | 11.4 |
| PEG 400 monooleate | Polyoxyethylene monooleate | 11.4 |
| Atlas G-2076 | Polyoxyethylene monopalmitate | 11.6 |
| S-511 | Polyoxyethylene monostearate | 11.6 |
| PEG 400 monostearate | Polyoxyethylene monostearate | 11.6 |
| Atlas G-3300 | Alkyl aryl sulphonate | 11.7 |
| Atlas G-1431 | Polyoxyethylene sorbitol lanolin derivative | 13 |

Examples of mixtures of emulsifiers with effective HLB values falling within the aforementioned ranges are given in the following table. It will be appreciated that the invention is not limited only to these emulsifiers and mixtures of emulsifiers. In particular, many alternative suitable mixtures of emulsifiers can be devised from the above table of individual emulsifiers and their respective HLB values or from similar data relating to other emulsifiers found, for example in Becher's book referred to herein, in particular at pages 235-238.

| Emulsifier mixtures for "water-in-oil" emulsions | | | | |
|---|---|---|---|---|
| Emulsifier | HLB value | % w/w in emulsifier mixture | Effective HLB value of each emulsifier | Net HLB value of mixture |
| Tween 80 | 15 | 30 | 4.5 | 7.5 |
| Span 80 | 14.3 | 70 | 3.0 | |

| Emulsifier mixtures for "oil-in-water" emulsions | | | | |
|---|---|---|---|---|
| Emulsifier | HLB value | % w/w in emulsifier mixture | Effective HLB value of each emulsifier | Net HLB value of mixture |
| Tween 80 | 15 | 70 | 10.5 | 11.8 |
| Span 80 | 4.3 | 30 | 1.3 | |
| Myrj 52 | 16.9 | 30 | 5.1 | 11.7 |
| Brij 30 | 9.5 | 70 | 6.6 | |
| Tween 20 | 16.7 | 41 | 6.8 | 11.9 |
| Span 20 | 8.6 | 59 | 5.1 | |
| Atlas G-2129 | 16.3 | 50 | 8.1 | 11.1 |
| Atlas G-2124 | 6.1 | 50 | 3.0 | |
| Tween 40 | 15.6 | 66.6 | 10.4 | 12.0 |
| Span 60 | 4.7 | 33.4 | 1.6 | |

[Tween 20 is polyoxyethylene sorbitan monolaurate
Tween 40 is polyoxyethylene sorbitan monopalmitate
Tween 80 is polyoxyethylene sorbitan monooleate
Span 60 is sorbitan monostearate
Span 80 is sorbitan monooleate
Brij 30 is polyoxyethylene lauryl ether
Myrj 52 is polyoxyethylene monostearate
Atlas G-2129 is polyoxyethylene monolaurate
Atlas G-2124 is diethylene glycol monolaurate (soap free).]

The proportion of the emulsifiers to be incorporated in the antiperspirant composition will be sufficient to effect adequate emulsification when the ingredients of the composition are emulsified. The emulsifier will accordingly form from 0.5% to about 10% by weight of the composition.

The antiperspirant composition of the invention also comprises water to enable an emulsion to be formed and to dissolve the antiperspirant agent when it is water soluble.

Although as we have stated, the polydimethylsiloxanes in view of their volatility do not remain long on the skin after application of the antiperspirant composition and therefore do not present a possible staining problem that can occur with oily non-volatile emollients, it is nevertheless possible to include in the composition according to the invention as an optional ingredient a small quantity of another emollient or carrier liquid in order to improve the capture by the skin of the antiperspirant agent.

Examples of suitable other emollients are carboxylic esters such as isopropyl myristate and isopropyl palmitate; liquid hydrocarbons such as tetradecane; fatty acids such as lauric acid and oleic acid; lanolin and its derivatives such as acetylated lanolin. Further suitable emollients are organic compounds containing multiple ester groups such as di-n-butyl phthalate, diethyl sebacate, di-isopropyl adipate, and ethyl ethylcarbomethyl phthalate.

Still other suitable emollients are polyethylene glycol monolaurate and ethoxylated or propoxylated butanol such as Ucon-HB-660 and Ucon HB-5100, hexylene glycol and diols such as 2-ethyl-1,3-hexane diol.

The emollients such as the foregoing can optionally be employed in amounts of from 0.5% to about 15%, preferably from 1% to 10% by weight of the antiperspirant composition.

Other ingredients commonly used in the art can optionally be incorporated in the antiperspirant composition according to the invention. Examples are perfumes, surfactants, germicidal compounds, such as hexachlorphene, 3,4,4'-trichlorocarbanilide, 3-trifluoromethyl-4,4'-dichlorocarbanilide and 3,5,4'-tribromosalicylanilide, anti-cholinergic materials such as trimethylacetyl scopolamine hydrochloride, and body malodour suppressant materials such as those which are the subject of Netherlands Patent Application No 7 409 704.

When the antiperspirant composition is to be dispensed in aerosol form from a pressurised pack device, a propellant can be included in the composition. The propellant can be either a liquefiable gas or a permanent gas or a mixture of liquefiable gas and permanent gas.

Examples of suitable liquefiable gaseous propellants are fluorohydrocarbons such as dichlorodifluoromethane (12); or blends such as trichlorofluoromethane plus dichlorodifluoromethane (11+12); or trichlorofluoromethane plus dichlorodifluoromethane plus symmetrical dichlorotetrafluoroethane (11+12+114); or trichlorofluoromethane plus dichlorodifluoromethane plus chlorodifluoromethane (11+12+22); or dichlorodifluoromethane plus symmetrical dichlorotetrafluoroethane (12+114); or chlorodifluoromethane plus symmetrical dichlorotetrafluoroethane (22+114); or dichlorodifluoromethane plus chlorodifluoromethane plus symmetrical dichlorotetrafluoroethane (12+22+114); and hydrocarbon propellants such as butane, isobutane, propane, pentane or isopentane or certain mixtures thereof.

Examples of suitable permanent gases are carbon dioxide, nitrogen and nitrous oxide.

The amount of the propellant employed is governed by normal factors as are well known in the aerosol art. It is sufficient to consider the propellant, when present, as constituting the balance of the composition of the invention that is not accounted for by the other components as detailed herein. The preferred limits of propellant when employing, for example, a single compartment aerosol container in which propellant and product are in admixture can therefore be from about 5% to about 95%, most preferably 15% to 80% by weight of the antiperspirant liquid composition.

The antiperspirant compositions according to this invention can also be dispensed in the form of a spray without use of a conventional propellant by using a container fitted with a finger-operated pump, for example, of the types disclosed in Netherlands Patent Application Nos. 7 415 900 and 7 608 562.

The antiperspirant composition can also be prepared in the form of creams, gels, pastes, suitable for spraying onto the skin.

When preparing antiperspirant liquid compositions according to the invention, in order to achieve a satisfactory thickened product which does not suffer from the problems sometimes encountered when using certain polymeric cellulosic thickeners or clay thickeners, referred to earlier in the specification, it is preferable first to dissolve the wax ingredient in the volatile polydimethylsiloxane and then to emulsify this solution with water and with other ingredients of the composition to form an emulsion. If this sequence is not followed, for example, when volatile polydimethylsiloxane wax, antiperspirant agents, emulsifier and water are mixed together simultaneously, adequate thickening may not be achieved without applying excessive shearing to the ingredients when preparing the emulsion.

The invention is illustrated by the following Examples illustrating antiperspirant liquid compositions which are sufficiently thickened so that when sprayed onto skin they do not form runs or dribble under the influence of gravity.

EXAMPLE 1

This example illustrates the preparation of an antiperspirant composition in the form of an oil-in-water emulsion.

The following ingredients were used to form an emulsion.

| | | % by weight |
|---|---|---|
| Volatile silicone 7207 | | 5.0 |
| Cetyl alcohol | | 2.0 |
| TWEEN 80 | emulsifier with HLB value of 11.8 | 2.4 |
| SPAN 80 | | 1.0 |
| Aluminum chlorhydrate | | 15.0 |
| Water | to | 100.0 |

A solution was first prepared of the cetyl alcohol in the volatile silicone 7207. This solution was emulsified with water and the TWEEN and SPAN emulsifying agents to form an emulsion.

The aluminium chlorhydrate was then dispersed in the emulsion so formed to provide an antiperspirant composition that was suitable for dispensing in aerosol form by means of finger-operated pumps, such as those described in Netherlands Patent Applications Nos 7 415 900 and 7 608 562.

When sprayed onto the skin of the axillae, the composition is retained at the point of application and does not run or dribble down the skin.

EXAMPLE 2

This example illustrates the preparation of an antiperspirant composition in the form of a water-in-oil emulsion.

The following ingredients should be used to form an emulsion.

| | % by weight |
|---|---|
| Volatile silicone 7207 | 40.0 |
| Cetyl alcohol | 1.0 |

| | | | % by weight |
|---|---|---|---|
| TWEEN 80 | Emulsifier with HLB value of 7.5 | | 1.0 |
| SPAN 80 | | | 2.4 |
| Aluminium chlorhydrate | | | 15.0 |
| Water | | to | 100 |

A solution was first prepared of the cetyl alcohol in the volatile silicone 7207. This solution was emulsified with water and the TWEEN and SPAN emulsifying agents to form an emulsion.

The aluminium chlorhydrate was then dispersed in the emulsion so formed to provide an antiperspirant composition that was suitable for dispersing in aerosol form by means of a finger-operated pump.

EXAMPLE 3

This example illustrates the preparation of an antiperspirant composition in the form of an oil-in-water emulsion for use with a pump spray applicator.

The following ingredients should be blended, the wax being first dissolved in the volatile silicone, before addition and blending of the remaining ingredients.

| | | | % by weight |
|---|---|---|---|
| Aluminium chlorhydrate | | | 15.0 |
| Volatile silicone F218 | | | 5.0 |
| POLAWAX | | | 3.0 |
| ATLAS G-2129 | Emulsifier with HLB value of 11.1 | | 1.5 |
| ATLAS G-2124 | | | 1.5 |
| Water | | to | 100 |

EXAMPLE 4

This example illustrates the preparation of a thickened liquid oil-in-water emulsion antiperspirant composition which is suitable for dispensing from a finger-operated pump spray device.

The following ingredients should be blended, the wax being first dissolved in the volatile silicone to form a thickened liquid product.

| | | | % by weight |
|---|---|---|---|
| Aluminium chlorhydrate | | | 4.0 |
| Calcium sodium alginate, a non-astringent moisture-absorbing polymeric material as described in Netherlands Patent Application No 7414561 | | | 4.0 |
| Volatile silicone F218 | | | 40.0 |
| Cetyl alcohol | | | 3.0 |
| TWEEN 20 | Emulsifier with HLB value of 11.9 | | 1.4 |
| SPAN 20 | | | 2.0 |
| Water | | to | 100 |

The following three examples illustrate formulations of antiperspirant aerosol products suitable for dispensing from an aerosol device.

EXAMPLE 5

The following ingredients should be blended, the wax being first dissolved in the volatile silicone, to form an oil-in-water emulsion aerosol concentrate.

| | | | % by weight |
|---|---|---|---|
| Aluminium chlorhydrate | | | 10.0 |
| Volatile silicone 7158 | | | 5.0 |
| Isopropyl myristate | | | 1.0 |
| Cetyl alcohol | | | 0.5 |
| TWEEN 40 | Emulsifier with HLB value of 12.0 | | 2.0 |
| SPAN 60 | | | 1.0 |
| Water | | to | 100 |

50 parts of this concentration should be mixed with 50 parts of propellant 114/12 (70:30) for dispensing from a pressurised pack.

EXAMPLE 6

95 parts by weight of the concentrate of Example 5 should be mixed with 5 parts by weight of nitrous oxide as the propellant for dispensing from a pressurised pack.

EXAMPLE 7

90 parts by weight of the concentrate of Example 5 should be filled into the upper compartment of the two compartment can described in British Pat. No. 1 390 927. 10 parts by weight of dichlorodifluoromethane (propellant F12) should be filled into the lower compartment. The product in the upper compartment can then be dispensed in aerosol form as an oil-in-water emulsion.

EXAMPLE 8

The example illustrates the formulation of a thickened antiperspirant liquid composition which is suitable for dispensing from hand operated spray devices such as those identified in Example 1.

The following ingredients were blended to form a thickened liquid composition, in the form of an oil-in-water emulsion, in the manner described in Example 1.

| | | | % by weight |
|---|---|---|---|
| Volatile silicone 7207 | | | 2.0 |
| Cetyl alcohol | | | 1.0 |
| TWEEN 80 | Emulsifier having HLB value of 11.8 | | 2.4 |
| SPAN 80 | | | 1.0 |
| Aluminium chlorhydrate | | | 15.0 |
| Water | | to | 100 |

EXAMPLE 9

This example illustrates the preparation of an antiperspirant composition in the form of an oil-in-water emulsion.

The following ingredients can be used to form an emulsion according to the method described in Example 1.

| | | | % by weight |
|---|---|---|---|
| Volatile silicone 7207 | | | 5.0 |
| Cetyl alcohol | | | 0.5 |
| TWEEN 80 | Emulsifier with HLB value of 11.8 | | 2.4 |
| SPAN 80 | | | 1.0 |
| Aluminium chlorhydrate | | | 15.0 |
| Water | | to | 100 |

EXAMPLE 10

This example illustrates the preparation of an antiperspirant composition in the form of a water-in-oil emulsion.

The following ingredients can be used to form an emulsion according to the method described in Example 2.

| | | % by weight |
|---|---|---|
| DC 200 Fluid (0.65 centistokes) | | 40.0 |
| Cetyl alcohol | | 1.0 |
| TWEEN 80 | Emulsifier with HLB value of 7.5 | 1.0 |
| SPAN 80 | | 2.4 |
| Aluminium chlorhydrate | | 15.0 |
| Water | to | 100 |

This example can be repeated using either DC 200 Fluid (1.0 centistokes) or DC 200 Fluid (5.0 centistokes) or mixtures of either or both of these volatile polydimethylsiloxanes with DC 200 Fluid (0.65 centistokes).

EXAMPLE 11

This example illustrates the preparation of an antiperspirant composition in the form of an oil-in-water emulsion for use with a pump spray applicator.

The following ingredients should be blended, the wax being first dissolved in the volatile silicone fluid, before addition with further blending of the remaining ingredients.

| | | % by weight |
|---|---|---|
| A polymeric aluminium compound as described in British Patent Application No 1401/76 | | 15.0 |
| DC 200 Fluid (1.0 centistokes) | | 5.0 |
| COSMOWAX | | 3.0 |
| ATLAS G-2129 | Emulsifier with HLB value of 11.1 | 1.5 |
| ATLAS G-2124 | | 1.5 |
| Water | to | 100 |

EXAMPLE 12

This example illustrates the preparation of a thickened liquid oil-in-water emulsion antiperspirant composition which is suitable for spraying onto the skin.

The following ingredients should be blended, the wax being dissolved first in the volatile silicone, to form a thickened liquid aerosol concentrate.

| | | % by weight |
|---|---|---|
| Aluminium chlorhydrate | | 10.0 |
| DC 200 Fluid (5.0 centistokes) | | 5.0 |
| Isopropyl myristate | | 1.0 |
| Polyethyleneglycol monostearate | | 0.5 |
| TWEEN 40 | Emulsifier with HLB value of 12.0 | 2.0 |
| SPAN 60 | | 1.0 |
| Water | to | 100 |

50 parts of this concentrate should be mixed with 50 parts of propellant 11/12 (65:35) for dispensing from a pressurised pack.

What is claimed is:

1. A spray antiperspirant composition in the form of an emulsion, consisting essentially of by weight of the composition:
   (i) from 2% to about 60% of a volatile polydimethylsiloxane having a viscosity of from 0.5 to 6 centistokes;
   (ii) from 0.1% to about 30% wax;
   (iii) from 0.2% to about 40% of an antiperspirant agent;
   (iv) from 0.5% to about 10% of an emulsifier; and
   (v) from about 40% to about 80% water; wherein the weight ratio of the volatile polydimethylsiloxane to wax is from 1:1 to 60:1.

2. A composition according to claim 1, wherein the volatile polydimethylsiloxane is a linear polydimethylsiloxane having the formula:

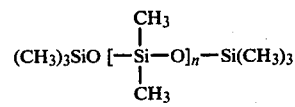

where n is an integer.

3. A composition according to claim 2, wherein the integer n has a value of from 1 to 5.

4. A composition according to claim 1, wherein the volatile polydimethylsiloxane is a cyclic polydimethylsiloxane having the formula:

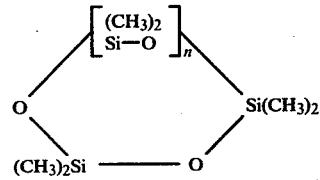

where n is an integer.

5. A composition according to claim 4, wherein the integer n has a value of from 1 to 4.

6. A composition according to claim 1, wherein the wax is a $C_{10}$–$C_{22}$ alkyl fatty alcohol having an average of from 0 to 50 ethylene oxide residues in the molecule.

7. A composition according to claim 1, wherein the wax is a $C_{10}$–$C_{22}$ alkyl ethoxylated fatty acid containing an average of from 1 to 50 ethylene oxide residues in the molecule.

8. A composition according to claim 1, wherein the wax is a triglyceride in which the esterifying acid is a $C_{10}$–$C_{22}$ alkyl fatty acid.

9. A composition according to claim 1, wherein the antiperspirant agent comprises an astringent metal salt.

10. A composition according to claim 9, wherein the astringent metal salt is aluminium chlorhydrate.

11. A composition according to claim 1, wherein the antiperspirant agent comprises a non-astringent moisture-absorbent polymeric material.

12. A composition according to claim 1, wherein the emulsifier has an HLB value of from 6.5 to 8.6.

13. A composition according to claim 1, wherein the emulsifier has an HLB value of from 10.5 to 13.

14. A process for preparing the antiperspirant liquid composition according to claim 1, which comprises forming a solution of the wax in the volatile polydimethylsiloxane and emulsifying the solution with water and the emulsion together with other ingredients of the composition, to form an emulsion.

* * * * *